(12) United States Patent
Zaveri et al.

(10) Patent No.: US 10,111,929 B1
(45) Date of Patent: Oct. 30, 2018

(54) GROWTH HORMONE RELEASING FACTOR ANALOGS AND USES

(71) Applicant: EZ IP, LLC, Castle Rock, CO (US)

(72) Inventors: Chanda Zaveri, Rancho Palos Verdes, CA (US); Joey D. Edge, Castle Rock, CO (US)

(73) Assignee: EZ IP, LLC, Castle Rock, CO (US)

( * ) Notice: Subject to any disclaimer, the term of this patent is extended or adjusted under 35 U.S.C. 154(b) by 0 days.

(21) Appl. No.: 15/482,592

(22) Filed: Apr. 7, 2017

(51) Int. Cl.
| | | |
|---|---|---|
| *A61K 38/25* | (2006.01) | |
| *A61K 38/08* | (2006.01) | |
| *C07K 7/06* | (2006.01) | |
| *C07K 7/00* | (2006.01) | |
| *C07K 14/60* | (2006.01) | |
| *C07K 14/00* | (2006.01) | |
| *A61K 47/48* | (2006.01) | |

(52) U.S. Cl.
CPC .......... *A61K 38/25* (2013.01); *A61K 47/4823* (2013.01); *C07K 14/60* (2013.01)

(58) Field of Classification Search
CPC .... A61K 38/25; A61K 38/08; A61K 47/4823; C07K 14/60; C07K 14/00; C07K 7/00; C07K 7/06
USPC .......... 530/300, 327, 328, 329; 514/1.1, 5.1, 514/21.5, 21.6, 21.7
See application file for complete search history.

(56) References Cited

U.S. PATENT DOCUMENTS

| | | | |
|---|---|---|---|
| 3,842,067 A | 10/1974 | Sarantakis | |
| 3,862,925 A | 1/1975 | Sarantakis et al. | |
| 3,972,859 A | 8/1976 | Fujino et al. | |
| 4,105,603 A | 8/1978 | Vale, Jr. et al. | |
| 6,696,248 B1 * | 2/2004 | Knappik | C07K 1/047 435/320.1 |
| 6,706,484 B1 * | 3/2004 | Knappik | C07K 1/047 435/320.1 |
| 7,713,927 B2 * | 5/2010 | He | A61K 8/64 514/1.1 |
| 2006/0063807 A1 | 3/2006 | Somers et al. | |
| 2016/0311855 A1 | 10/2016 | Dong | |

FOREIGN PATENT DOCUMENTS

WO     2016191865 A1    12/2016

OTHER PUBLICATIONS

R.A. Houghten, Proc. Natl. Acad. Sci. USA 82, 5131-5135 (1985).
R.E. Hileman et al., Glycosaminoglycan-protein interactions: definition of consensus sites in glycosaminoglycan binding proteins, BioEssays, 20, 156-167 (1998).
International Search Report and Written Opinion for PCT/US18/26425 dated Aug. 7, 2018.

* cited by examiner

*Primary Examiner* — Julie Ha
(74) *Attorney, Agent, or Firm* — Elevated IP, LLC

(57) ABSTRACT

Growth hormone releasing factor (GHRF) analogs that can be used to induce endogenous growth hormone secretion are disclosed, as well as pharmaceutical compositions comprising the GHRF analogs and methods of using the GHRF analogs.

19 Claims, 5 Drawing Sheets

GROWTH HORMONE RELEASING FACTOR ANALOGS AND USES

CROSS-REFERENCE TO RELATED APPLICATIONS

None.

BACKGROUND

Established anti-aging therapies have dearly shown that science can intercede in the aging process to maximize health and longevity. And indeed, many scientists now regard aging as both a treatable and reversible condition.

Central to the popular acceptance of anti-aging therapy has been the creation of a practical working theory on aging. This theory associates the body's progressive inability at self-repair with hormonal deficiency. The application of this idea, and the unprecedented popularity of hormonal supplementation, testifies to the validity of hormone replacement therapy as an effective means of restoring the body's resilience and ability to self-repair.

Human Growth Hormone, or HGH, has emerged at the forefront of anti-aging therapy. The hormone's ascension has been buttressed by an impressive collection of basic science and clinical findings. The hormone's ability to promote cell regeneration, stimulate tissue repair and bolster the immune system is critical in this forum, since virtually all of the complications of aging stem from the body's inability to repair and replace cells as it loses them.

Theories of Aging

The precise reason why Growth Hormone (GH) levels decrease with advancing age is unknown. However, there are a number of theories that begin to explain this depression within the context of an organism's natural aging process. The theories are as follows:

Oxidative Stress Theory asserts that the body's absorption of oxygen is intricately related to the aging process. The more food a person or animal consumes, the more oxygen the body needs to break it down into energy, and the more rapidly the animal ages due to the creation of free radicals that impair cell function.

The Genetic Theory of Aging asserts that as genetic damage accumulates simply as a consequence of living (i.e. via ongoing cell repair and division), the body's overall efficiency decreases, with aging as a consequence.

The Theory of Somatopause (or Cellular Senescence) asserts that cells are pre-programmed to either die after a finite number of divisions or simply go dormant. As the cells lapse into this phase of their cycle, the efficiency of the organism to maintain its vital functions decreases, until ultimately the organism itself dies.

The Hormonal Theory of Aging asserts that aging is linked to a decline in the body's secretion of a variety of hormones without losing the ability to respond to these hormones. This is the principle basis for hormone replacement therapy with GH.

Growth Hormone

Growth hormone (G H) is a 191 amino acid long protein that is synthesized and secreted by the pituitary gland found at the base of the brain. The hormone enters the bloodstream in pulses, predominantly at night, and is then quickly metabolized by the liver into the insulin-like growth factors, IGF-1 and IGF-2. (See FIG. 1)

The natural depression of GH secretion with age starts in the mid-twenties and continues as we grow older. By the age of 60, GH levels are typically 15-20% of what they were when a person was in their twenties, sometimes even less.

People that have taken HGH by injection have noticed an overall improvement in their general well-being and vitality, with the following specific reports:
Stronger bones
Enhanced immune system
Accelerated wound healing/tissue regeneration
Decrease in total cholesterol
Increase in muscle mass without exercise
Loss of body fat without exercise
Weight Loss
Improved blood pressure
Younger, more durable skin with fewer wrinkles
Increased energy
Enhanced sexual performance and libido
Increased cardic output
Enhanced exercise performance
Improved mood
Improved memory
Improved sleep pattern
Organ regeneration
Regrowth of lost hair
Insulin-Like Growth Factors, IGF-1 & IGF-2

GH is released into the bloodstream in small pulsatile bursts during the day that peak during deep sleep. Since the longevity of GH in the bloodstream is very short after its secretion, accurately measuring GH levels directly can be very cumbersome. Consequently, measurement of GH levels is typically achieved indirectly, by measuring for levels of another hormone called Insulin-like Growth Factor 1 (IGF-1).

IGF-1 is produced by the liver in response to circulating GH and remains relatively constant throughout the day in contrast to GH. As such, IGF-1 levels are the standard means to evaluate how much GH the pituitary is releasing, especially when looking for a change over time.

The goal of GH replacement therapy by injection for individuals over 50 is to raise IGF-1 levels to within the range of healthy young adults, which is around 350 µg/m L.

HGH Replacement Supplementation Vs. GH Releasing Factors

It is helpful to understand the relative benefits and risks of HGH replacement supplementation by injection versus the use of an agent that stimulates the release of GH.

GH replacement supplementation by injection can offer substantial benefits, as presented earlier. As with any hormone replacement or supplementation, however, the converse is also true. Poorly monitored HGH supplementation may be associated with allergic reactions, carpal tunnel syndrome, irregularities of bone growth (acromegaly), diabetes and swelling.

Use of a GH Releasing Factor (GHRF), or secretagogue, minimizes the risk of complications associated with GH injections. This decrease in risk is achieved by eliminating the shock of pharmacologic GH injections and the resultant steep increase in IGF-1 levels. By using a GHRF, IGF-1 levels increase more slowly and plateau at levels far below the extremes of GH replacement therapy. Furthermore, healthy advocates of GH supplementation can reasonably use an oral GHRF agent without a physician's involvement.

SUMMARY

The present invention relates to synthetic growth hormone releasing factors (GHRFs) or GHRF analogs that are novel GH secretagogues, which promote the release of endogenous growth hormone (GH) in mammals, particularly humans, needing elevation of serum growth hormone levels.

In an aspect, a growth hormone releasing factor (GHRF) analog comprises a sequence of $Xaa_1$-D-2-Nal-Trp-His-Trp-D-Phe-$Xaa_2$, wherein $Xaa_1$ is an amino acid residue selected from D-Ala, D-Val and Gly and $Xaa_2$ is an amino acid residue selected from Lys and Arg, or a pharmaceutically acceptable salt thereof. In an embodiment, $Xaa_1$ is an amino acid residue selected from D-Ala and D-Val and $Xaa_2$ is an amino acid residue selected from Lys and Arg. In an embodiment, $Xaa_1$ is D-Ala and $Xaa_2$ is an amino acid residue selected from Lys and Arg. In an embodiment, $Xaa_1$ is D-Ala and $Xaa_2$ is Lys.

In an aspect, a growth hormone releasing factor (GHRF) analog comprises a sequence of D-Ala-D-2-Nal-Trp-His-Trp-D-Phe-Lys.

In an aspect, a growth hormone releasing factor (GHRF) analog consists of a sequence of H-D-Ala-D-2-Nal-Trp-His-Trp-D-Phe-Lys-$NH_2$.

In an embodiment, a GHRF analog has a weight average molecular weight of 700 Daltons to 1000 Daltons, or 750 Daltons to 950 Daltons, or 790 Daltons to 900 Daltons.

In an embodiment, a GHRF analog has an optical purity of at least 90%, or at least 95%, or at least 98%, or at least 99%, or at least 99.5%, or at least 99.9%.

In some embodiments, a GHRF analog of the present invention is formulated as a conjugate or proteoglycan. In the conjugate or proteoglycan, the GHRF analog is chemically bound (e.g., covalently bound or ionically bound) to a molecule or moiety to provide one or more chemical or physical properties differing from those of the GHRF analog alone. For example, a GHRF analog-conjugate may provide a higher level of absorption in a subject or improved storage stability relative to the GHRF analog alone.

In an embodiment, the GHRF analog is conjugated to a compound selected from the group consisting of glycosaminoglycans (GAGS), glycosaminoglycan-like (GAG-like) polysaccharides, oligosaccharides and combinations thereof. In an embodiment, the GAG is selected from the group consisting of chondroitin sulfate, dermatan sulfate, keratin sulfate, heparin, heparin sulfate, hyaluronan (hyaluronic acid) and pharmaceutically acceptable salts thereof.

In some embodiments, the GHRF analog is formulated as a pharmaceutical composition comprising a GHRF analog, a GHRF analog-conjugate, or a pharmaceutically acceptable salt of the GHRF analog and one or more pharmaceutically acceptable carriers, excipients and/or diluents.

In some embodiments, a pharmaceutical composition of the present invention comprises a GHRF analog, a GHRF analog-conjugate, or a pharmaceutically acceptable salt of the GHRF analog; one or more pharmaceutically acceptable carriers, excipients and/or diluents; and one or more amino acids, which may be present in a concentration from 300 mg to 600 mg, or 350 mg to 550 mg, or 380 mg to 500 mg. Suitable amino acids for use in the pharmaceutical compositions include, but are not limited to, amino acids selected from the group consisting of lysine, argenine, ornithine, glutamine and combinations thereof.

In an embodiment, a pharmaceutical composition is administered to a subject 1-12 times per day, or 1-6 times per day, or 1-3 times per day, or twice daily, or once daily.

In an aspect, a method of inducing growth hormone secretion in a subject in need thereof comprises administering to the subject a therapeutically effective amount of a GHRF analog, a GHRF analog-conjugate, or a pharmaceutical salt of the GHRF analog. In an embodiment, the GHRF analog, conjugate or pharmaceutically acceptable salt is administered at a daily dose of 50 ng/Kg to 750 ng/Kg, or 100 ng/Kg to 500 ng/Kg, or 150 ng/Kg to 350 ng/Kg.

In an embodiment, the GHRF analog, conjugate or pharmaceutically acceptable salt is administered, for example as a pharmaceutical composition, intravenously, orally, sublingually, transdermally, subcutaneously, mucosally, intramuscularly, intranasally, intrapulmonary, parenterally, intrarectally, intravaginally or topically. In an embodiment, the GHRF analog, conjugate or pharmaceutically acceptable salt is administered, for example as a pharmaceutical composition, orally or mucosally. In an embodiment, the GHRF analog, conjugate or pharmaceutically acceptable salt is administered, for example as a pharmaceutical composition, as an oral spray, solution or suspension.

DETAILED DESCRIPTION

Figure 1:
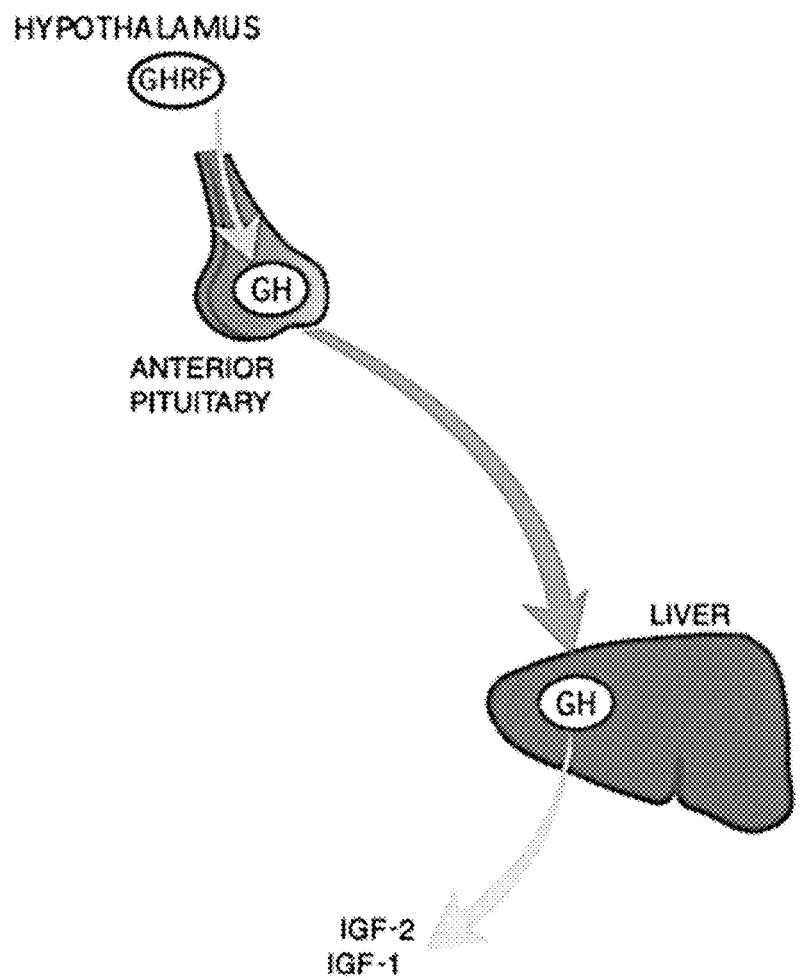
FIG. 1 is a schematic of the growth hormone mechanism.

In general, the terms and phrases used herein have their art-recognized meaning, which can be found by reference to standard texts, journal references and contexts known to those skilled in the art. The following definitions are provided to clarify their specific use in the context of this description.

An "amino acid" is a molecular building block of protein. An "amino acid residue" is the simplest discreet unit or monomer of a protein chain.

A "hormone" is a chemical messenger that initiates a reaction in or near cells.

"Human growth hormone" (HGH) is a hormone comprising 191 amino acid residues. HGH is secreted by the anterior pituitary, is responsible for somatic growth, and contributes to the regulation of metabolism, the regeneration of tissues and immune system function.

A "growth hormone releasing factor" (GHRF) refers to the endogenous hypothalamic GH secretagogue, from any species.

A "secretagogue" is a releasing factor that stimulates the secretion of a chemical, usually a hormone.

A "growth hormone releasing factor (GHRF) analog" is a synthetic, non-naturally occurring (exogenous) secretagogue.

A "conjugate" is a chemical entity formed by coupling or bonding two chemical moieties. In an embodiment, a conjugate is a chemical molecule formed by covalently or ionically bonding two chemical moieties. In an embodiment, a proteoglycan is a conjugate formed by covalently or ionically bonding a protein/peptide and a glycan.

"Pharmaceutically acceptable salts" include both acid and base addition salts.

"Pharmaceutically acceptable acid addition salt" refers to those salts which retain the biological effectiveness and properties of the free bases and which are not biologically or otherwise undesirable, formed with inorganic acids including but not limited to hydrochloric acid, hydrobromic acid, sulfuric acid, sulfamic nitric acid, phosphoric acid and the like, and organic acids such as acetic acid, propionic acid, glycolic acid, pyruvic acid, lactic acid, oxalic acid, maleic acid, malic acid, maloneic acid, succinic acid, fumaric acid, tartaric acid, citric acid, stearic acid, ascorbic acid, benzoic acid, cinnamic acid, mandelic acid, methanesulfonic acid, ethanesulfonic acid, p-toluenesulfonic acid, salicyclic acid, naturally occurring amino acids and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

"Optical isomers", "diastereomers", and "geometric isomers" of some of the compounds represented by the formulae described herein are comprehended to be within the scope of the instant invention, as well as racemic and resolved enantiomerically pure forms and pharmaceutically acceptable salts thereof.

"Optical purity" is a comparison of the optical rotation of a pure sample of unknown stereochemistry versus the optical rotation of a sample of pure enantiomer. It is expressed as a percentage, where 0% indicates a 50/50 racemic mixture and 100% indicates an enantiomerically pure sample.

Methods of Peptide Synthesis

One method of producing GHRF analogs involves chemical synthesis of the peptide. This can be accomplished using solid phase methodologies well known to those skilled in the art. (See, e.g., Stewart, J. M. & Young, J. D. "Solid Phase Peptide Synthesis" Pierce Chemical Co, Rockford, Ill., 1984; Merrifield, J. Am. Chem. Soc., 85:2149 1964; Houghten, Proc. Natl. Acad. Sci. USA 82:5132 1985; and U.S. Pat. Nos. 4,105,603; 3,972,859; 3,842,067; and 3,862,925).

Solid phase synthesis begins at the carboxy-terminus of the putative peptide by coupling a protected amino acid to a suitable resin (e.g. chloromethylated polystyrene resin). After removal of the α-amino protecting group with, for example, trifluoroacetic acid (TFA) in methylene chloride and neutralizing in, for example TEA, the next α-amino- and sidechain protected amino acid in the synthesis is added. The remaining α-amino- and, if necessary, side-chain-protected amino acids are then coupled sequentially in the desired order by condensation to obtain an intermediate compound connected to the resin. Alternatively, some amino acids may be coupled to one another forming a peptide prior to addition of the peptide to the growing solid phase polypeptide chain.

The condensation between two amino acids, or an amino acid and a peptide, or a peptide and a peptide can be carried out according to the usual condensation methods such as the azide method, mixed acid anhydride method, DCC (N,N'-dicyclohexylcarbodiimide) or DIPC (N,N'-diisopropylcarbodiimide) methods, active ester method (p-nitrophenyl ester method), BOP benzotriazole-1-yl-oxy-tris (dimethylamino) phosphonium hexafluorophosphate method, N-hydroxysuccinic acid imido ester method, etc., and Woodward reagent K method.

Common to chemical syntheses of peptides is the protection of any reactive side-chain groups of the amino acids with suitable protecting groups. Ultimately, these protecting groups are removed after the desired polypeptide chain has been sequentially assembled. Also common is the protection of the α-amino group on an amino acid or a fragment while that entity reacts at the carboxyl group followed by the selective removal of the α-amino-protecting group to allow subsequent reaction to take place at that location. Accordingly, it is common in polypeptide synthesis that an intermediate compound is produced which contains each of the amino acid residues located in the desired sequence in the peptide chain with various of these residues having side-chain protecting groups attached. These protecting groups are then commonly removed substantially at the same time so as to produce the desired resultant product following removal from the resin.

Suitable protective groups for protecting the α- and ε-amino side chain groups are exemplified by benzyloxy-carbonyl (CBZ), isonicotinyloxycarbonyl (iNOC), O-chlorobenzyloxycarbonyl (2-Cl-CBZ), p-nitrobenzyloxycarbonyl $Z(NO_2)$, p-methoxybenzyloxycarbonyl Z(OMe), t-butoxycarbonyl, (BOC), t-amyloxycarbonyl (AOC), isoborrnyloxycarbonyl, adamatyloxycarbonyl, 2-(4-biphenyl)-2-propyloxycarbonyl (BPOC), 9-fluorenylmethoxycarbonyl (FMOC), methylsulfonyiethoxycarbonyl (Msc), trifluoroacetyl, phthalyl, formyl, 2-nitrophenylsulphenyl (NPS), diphenylphosphinothioyl (Ppt), dimethylophosphinothioyl (Mpt) and the like.

Protective groups for the carboxy functional group are exemplified by benzyl ester (OBzl), cyclohexyl ester (Chx), 4-nitrobenzyl ester (ONb), t-butyl ester (OtBu), 4-pyridylmethyl ester (OPic), and the like. It is often desirable that specific amino acids such as arginine, cysteine, and serine possessing a functional group other than amino and carboxyl groups are protected by a suitable protective group. For example, the guanidino group of arginine may be protected with nitro, p-toluenesulfonyl, benzyloxycarbonyl, adamantyloxycarbonyl, p-methoxybenzenesulfonyl, 4-methoxy-2, 6-dimethylbenzenesulfonyl (Mds), 1,3,5-trimethylphenysulfonyl (Mts), and the like. The thiol group of cysteine may be protected with p-methoxybenzyl, triphenylmethyl, acetylaminomethyl ethylcarbamoyle, 4-methylbenzyl, 2,4,6-trimethy-benzyl (Tmb) etc., and the hydroxyl group of serine can be protected with benzyl, t-butyl, acetyl, tetrahydropyranyl and the like.

After the desired amino acid sequence has been completed, the intermediate peptide is removed from the resin support by treatment with a reagent, such as liquid HF and one or more thio-containing scavengers, which not only cleaves the peptide from the resin, but also cleaves all the remaining side-chain protecting groups. Following HF cleavage, the peptide residue is washed with ether, and extracted from the resin by washing with aqueous acetonitrile and acetic acid.

Amino Acid Substitutions

It is a well-established principle of protein and peptide chemistry that certain amino acid substitutions, entitled "conservative" amino acid substitutions, can frequently be made in a protein or a peptide without altering either the conformation or the function of the protein or peptide. Conservative substitutions may be employed in the synthesis of proteins, peptides or analogs disclosed herein. Accordingly, peptides having conservative amino acid substitutions are within the scope of the present invention. Such changes include substituting any of isoleucine (I), valine (V), and leucine (L) for any other of these amino acids; aspartic acid (D) for glutamic acid (E) and vice versa; glutamine (O) for asparagine (N) and vice versa; and serine (S) for threonine (T) and vice versa. The above-mentioned substitutions are not the only amino acid substitutions that can be considered "conservative." Other substitutions can also be considered conservative, depending on the environment of the particular amino acid. For example, glycine (G) and alanine (A) can frequently be interchangeable, as can be alanine and valine. Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pKs of these two amino acid residues are not significant. Cysteine (C) can frequently be replaced by serine (S) when cysteine's capacity to form disulfide bonds is either undesirable or unneeded. Still other changes can be considered "conservative" in particular environments.

Pharmaceutical Compositions

Another aspect of the present invention is pharmaceutical compositions that include GHRF analogs according to the present invention. In general, a pharmaceutical composition of the present invention comprises a GHRF analog, conjugate or pharmaceutically acceptable salt in a therapeutically effective amount and a pharmaceutically acceptable carrier, excipient or diluent.

The GHRF analogs may be formulated into the pharmaceutical compositions as neutral or salt forms. Pharmaceutically acceptable nontoxic salts include the acid addition salts (formed with the free amino groups) and which are formed with inorganic acids such as, for example, hydrochloric or phosphoric acids, or organic acids such as acetic, oxalic, tartaric, mandelic, and the like. Base addition salts may be derived from inorganic bases such as, for example, sodium, potassium, ammonium, calcium, or ferric hydroxides, and such organic bases as isopropyl amine, 2-ethyl-amino ethanol, histidine, procaine, and the like.

The therapeutically effective amount can be determined by one of ordinary skill in the art, with reference to the dosages described herein.

Conventional pharmaceutically acceptable carriers known in the art can include alcohols, e.g., ethyl alcohol, serum proteins, cholesterol, human serum albumin, liposomes, buffers such as phosphates, water, sterile saline or other salts, electrolytes, glycerol, hydroxymethylcellulose, propylene glycol, polyethylene glycol, polyexyethylenesorbitan, other surface active agents, vegetable oils, and conventional anti-bacterial or anti-fungal agents, such as parabens, chlorobutanol, phenol, sorbic acid, and the like. A pharmaceutically acceptable carrier within the scope of the present invention meets industry standards for sterility, isotonicity, stability, and non-pyrogenicity.

The active ingredient is often mixed with diluents or excipients that are physiologically tolerable and compatible with the active ingredient. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH-buffering agents, and the like. For a more detailed description of the foregoing see a standard pharmaceutical text such as Remington's Pharmaceutical Sciences, Mack Publishing Co. Easton, Pa. (1970).

Oral formulations may include excipients such as pharmaceutical grade mannitol, lactose, starch, magnesium stearate, sodium saccharin, cellulose; magnesium carbonate, and the like. These compositions take the form of solutions, suspensions, tablets, pills, capsules, sustained-release formulations, or powders, and contain 0.5% to 15% of active ingredient, or 1% to 12% of active ingredient or 2%-10% of active ingredient, or 2.5% to 8% of active ingredient.

In an embodiment, a solution or suspension may be formed by the combination of an effervescent tablet or powder with a liquid. An effervescent tablet or powder is designed to dissolve and produce bubbling when the tablet or powder comes into contact with water or another liquid. The bubbling is due to release of carbon dioxide when sodium bicarbonate and citric acid, or other appropriate chemicals, in the tablet or powder dissolve in the liquid and react.

Methods of Use

The compounds of this invention are shown to induce release of growth hormone and IGF-1. It is known to those skilled in the art that there are many uses for growth hormone and the IGFs. Therefore administration of the GHRF analogs and pharmaceutical compositions of this invention for purposes of stimulating the release of endogenous growth hormone or IGF-1 can have the same effects or uses as growth hormone or the IGFs themselves. These uses of growth hormone and IGF-1 include, but are not limited to, slowing, stopping or reversing aging; strengthening bones; treating osteoporosis; accelerating bone fracture repair; stimulating the immune system; accelerating wound healing; decreasing total cholesterol; increasing muscle mass; stimulating weight loss; treating obesity; treating high blood pressure; improving skin texture; increasing energy; treating fatigue; enhancing sexual performance; increasing libido; increasing cardiac output; improving exercise performance; improving mood; treating depression; improving memory; treating cognitive degeneration; improving sleep patterns; regenerating tissue; and stimulating hair growth.

Administration

GHRF analogs and pharmaceutical compositions according to the present invention can be administered by a number of routes. When used for wound healing, they are typically administered topically to the skin or other mucous membranes. However, when they are administered as immunostimulants or as growth factors to stimulate pituitary or hypothalamus function, they can be administered by other routes, such as intravenously, orally, sublingually, transdermally, subcutaneously, mucosally, intramuscularly, intranasally, intrapulmonary, parenterally, intrarectally, intravaginally, intradermally or topically. In an embodiment, oral administration may be accomplished by an oral spray, solution or suspension, e.g., where the solution or suspension is formed by the combination of an effervescent tablet or powder with a liquid.

The dosages to be administered can be determined by one of ordinary skill in the art depending on the clinical severity of the disease, the age, sex and weight of the patient, the exposure of the patient to conditions that may affect the course of wound healing, the existence or nonexistence of underlying systemic problems such as diabetes, impaired circulation, and immunocompromised status, and other pharmacokinetic factors generally understood in the art, such as liver and kidney metabolism. The interrelationship of dosages for animals of various sizes and species and humans based on $mgim^3$ of surface area is described by E. J. Freireich et al., "Quantitative Comparison of Toxicity of Anticancer Agents in Mouse, Rat, Hamster; Dog, Monkey and Man," Cancer Chemother, Rep. 50:219-244 (1966). Adjustments in the dosage regimen can be made to optimize the therapeutic response. Doses can be divided and administered on a daily basis or the dose can be reduced proportionally depending on the therapeutic situation.

Methods according to the present invention can be used to treat humans or socially or economically important animal species such as dogs, cats, horses, sheep, cows, goats, or pigs. Methods according to the present invention are not limited to use in humans.

The invention is illustrated by the following Examples. These Examples are for illustrative purposes only and are not intended to limit the invention.

Example 1: Development of a New Growth Hormone Releasing Factor

This Example describes the development of a new growth hormone releasing factor analog, particularly, an oral GHRF analog that could safely offer a viable alternative to HGH injections. The new GHRF analog is referred to herein as HTA-8.

HTA-8

HTA-8 peptide sequence:

H-D-Ala-D-2-Nal-Trp-H is-Trp-D-Phe-Lys-N $H_2$

Standard three letter codes are used to designate the amino acids with a "D" placed before the three-letter code to signify the dextrorotatory enantiomer. Accordingly, HTA-8 contains the following seven amino acids:

(D-Alanine)-(D-2-Naphthylalanine)-Tryptophan-Histidine-Tryptophan-(D-Phenylalanine)-Lysine.

Figure 2:
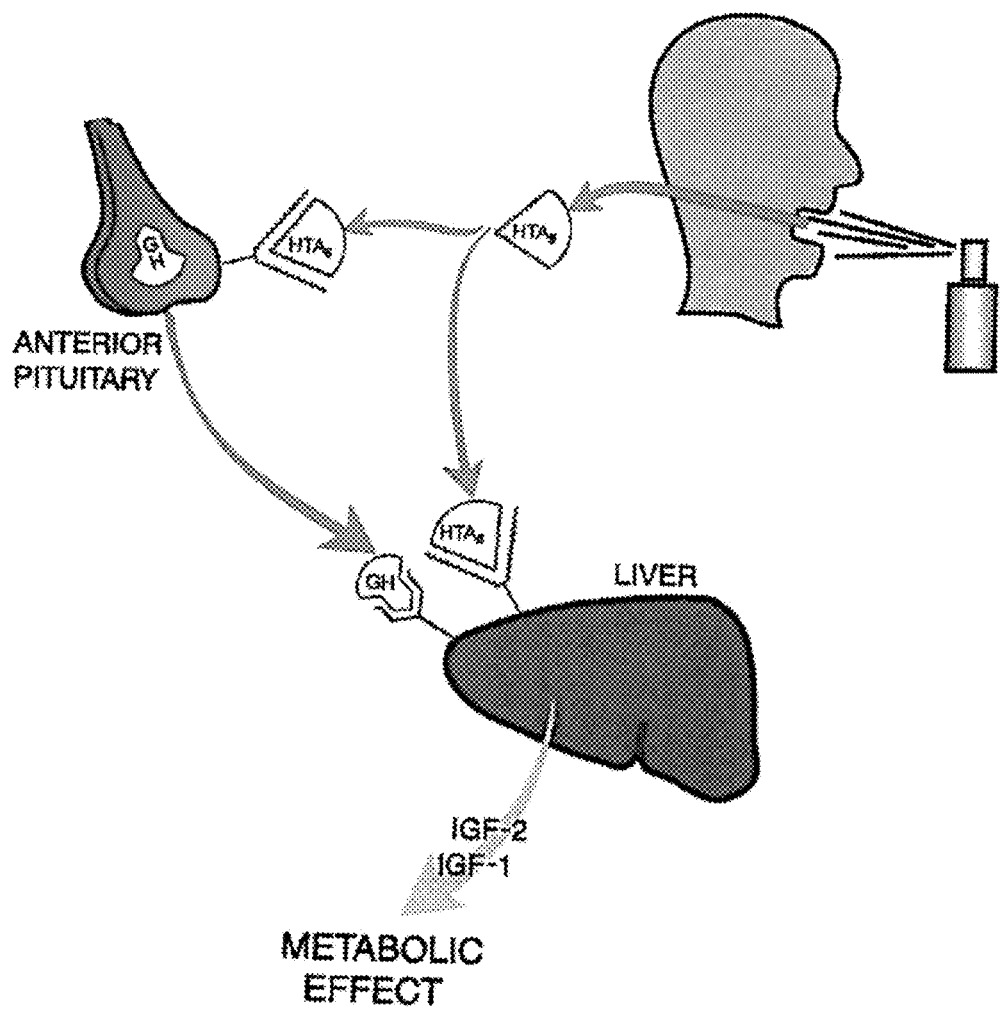
FIG. 2 is a schematic of the HTA-8 mechanism.

HTA-8 is a small protein chain that behaves like GHRF1 on the pituitary to stimulate the release of GH. HTA-8 also binds to GH receptors in the liver. (See FIG. 2) The end result is that a low dose of HTA-8 has a similar efficacy to higher doses of HGH injection. HTA-8 is not a GH precursor.

Example 2: Human Clinical Testing

Two challenges were being considered at the beginning of the human clinical trial. The first challenge was to document the stand-alone efficacy of HTA-8 as a new growth hormone releasing factor. The second was to determine if HTA-8 could be combined with other common releasing factors to create an even better result. As such, two separate trials were conducted.

Trial #1/HTA-8: Ten individuals ranging in age from 30 to 69 years were given 30 ng of HTA-8 in the form of an aerosolized oral spray before bed, over a 30-32 day period.

Trial #2/HTA-8+: Fifteen individuals ranging in age from 38 to 70 years of age were given an effervescent tablet to take once daily over a 25-36 day period that contained 20 ng of HTA-8 in combination with 1200 mg each of the amino acids lysine and arginine. (Previous published experimentation has shown that the combination of lysine and arginine in the doses used in Trial #2 is an effective GH releasing factor.)

HTA-8 & IGF-1

The principal hormone measured in order to establish whether there is an increase in growth hormone secretion is IGF-1. IGF-1 concentrations and total cholesterol levels were determined by collecting participant blood samples at the beginning of the studies and at their conclusion.

The results of Trial #1 confirm that HTA-8 alone is a bona fide, stand-alone GHRF. Furthermore, it also appears that HTA-8 in combination with the amino acids lysine and arginine is capable of increasing IGF-1 levels in excess of HTA-8 alone (Trial #2). These results confirm that GH secretion is increased with HTA-8.

IGF-1 levels in HTA-8 Trial #2 increased from 169.8 μg/mL to 202.4 μg/mL on average. The maximum IGF-1 level measured in all clinical trial participants after the study period was 410 μg/mL in a 30 year-old male in HTA-8 Trial #1.

Figure 3:
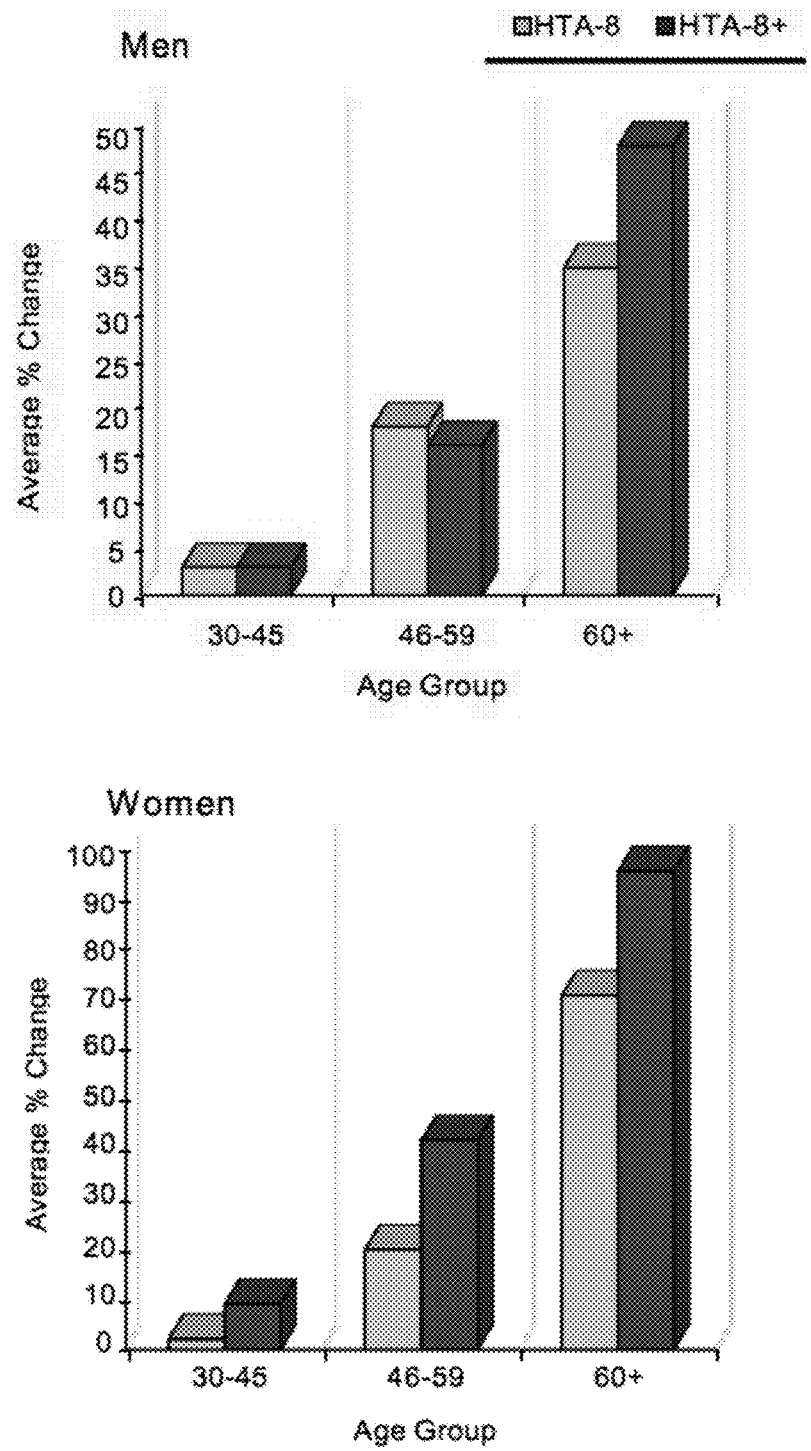
FIG. 3 shows graphs of average percent change of IGF-1 by age group and sex during Trial #1 and Trial #2.

In addition, the following observations may be made from the IGF-1 data in FIG. 3:

The change in IGF-1 concentrations in the presence of HTA-8 alone or in combination with amino acids was found to be both age and sex dependent. A more substantial change in IGF-1 concentrations was noted with advancing age groups, regardless of sex.

A woman's IGF-1 response to HTA-8 with or without amino acids was calculated to be greater than a man's response. This difference in IGF did not result in significant body mass changes between the sexes.

It should be noted that across all clinical trial participants, the greatest percent change in IGF-1 concentrations was observed in participants that started with very low baseline IGF-1 concentrations (e.g. 21 ng/mL).

Total Cholesterol

Figure 4:
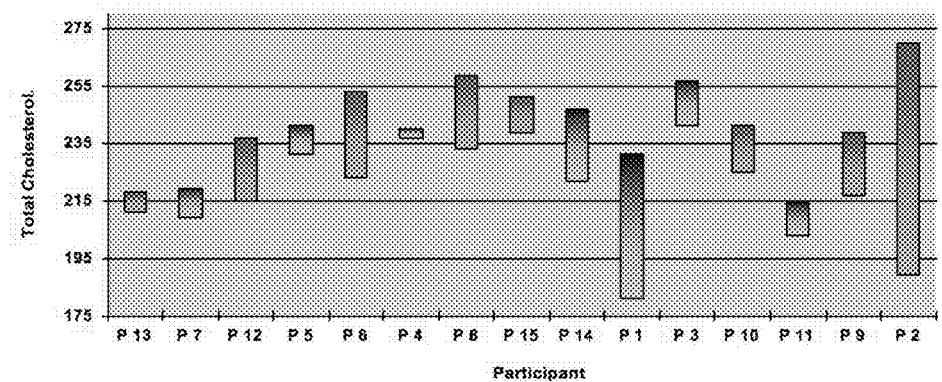
FIG. 4 is a graph showing decreases in total cholesterol during Trial #2.

The National Cholesterol Education Program (NCEP) has been advocating that people maintain a low total blood cholesterol level as a means to minimize the potential for cardiovascular disease. Current NCEP guidelines recommend that adult individuals work toward reducing total cholesterol levels to at least 200 mg/mL as part of a healthful lifestyle. The majority of clinical trial participants using HTA-8 (with or without amino acids) demonstrated a clinically significant decrease in their total cholesterol levels over the study period, in the absence of additional measures. Study results for Trial #2 participants are presented in FIG. 4, where the change in total cholesterol for each participant is represented as a shift from the top (darker) area of the bar to the bottom (lighter) area of the bar.

Bone Density

An increase in bone density decreases the chance of fracture and osteoarthritis. Bone density is a particularly important issue as the body ages, regardless of sex. During the Clinical Trials, radial bone density was measured using an ultrasonographic technique.

The average increase in bone density for subjects taking HTA-8 alone was 6.8%. The average increase in bone density for subjects taking HTA-8 plus amino acids was 12.6%.

Figure 5:
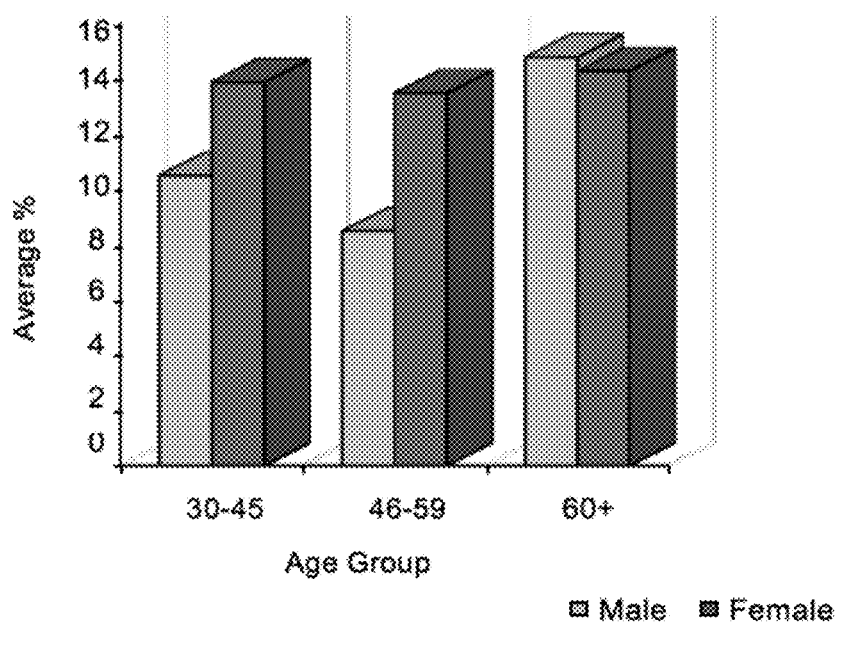
FIG. 5 is a graph of average percent increase in radial bone density by age group and sex during Trial #2.

FIG. 5 illustrates the bone density increases measured for men and women in Clinical Trial #2. Note that neither sex nor age group has a significant influence on the activity of HTA-8 to affect bone density.

Lean Body Mass/Adipose Tissue Mass

One of the basic roles of growth hormone and IGF-1 is in the regulation of insulin levels, glucose metabolism and fatty tissue metabolism.

Figure 6:
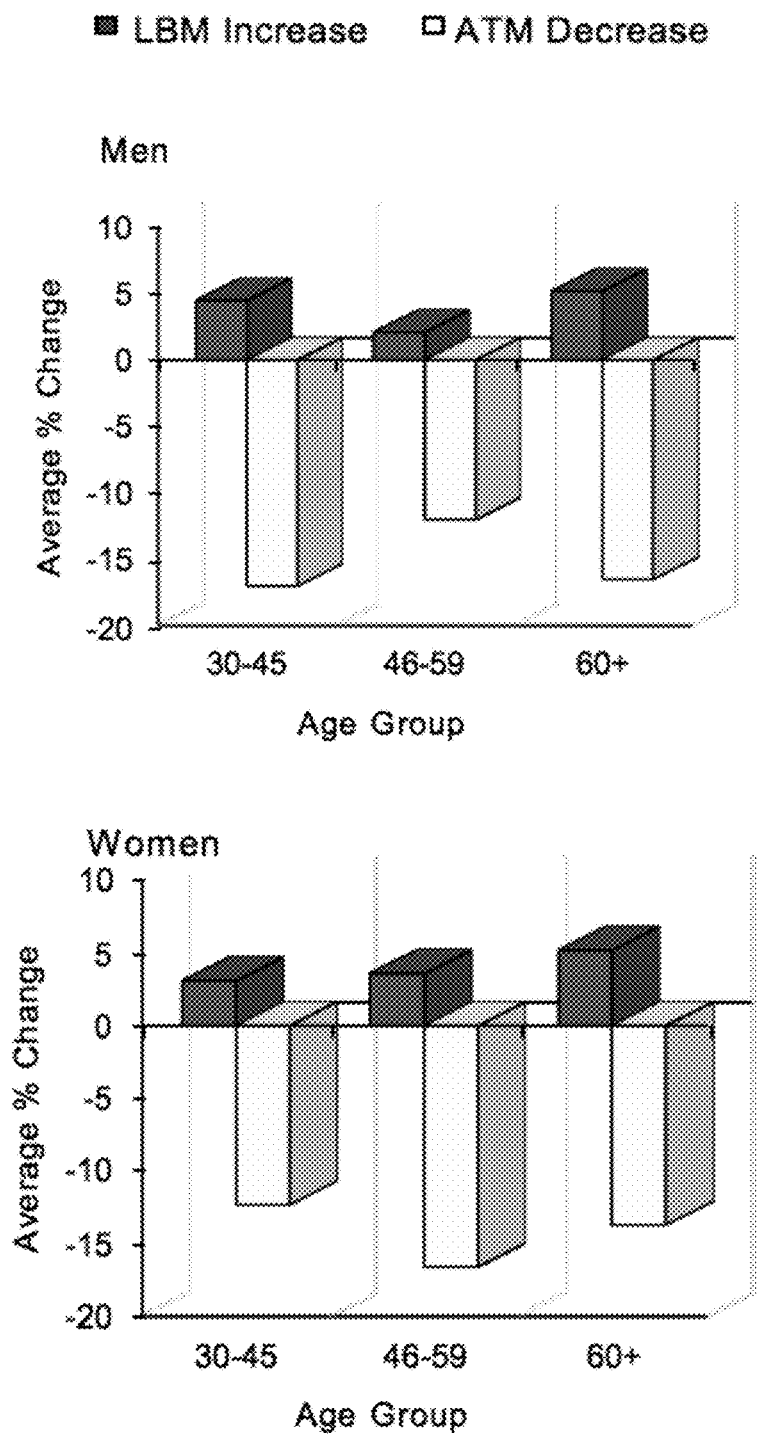
FIG. 6 shows graphs of average percent change of lean body mass (LBM) and adipose tissue mass (ATM) by age group and sex during Trial #2.

An increase in lean muscle mass and a decrease in adipose tissue mass was recorded for all study participants in both clinical trials using an ultrasound-based body composition analysis. The noted increase in muscle mass and decrease in adipose tissue mass at the conclusion of the study period was slightly more than doubled for study participant's given HTA-8 with amino acids. Participants lost an average of 13.2% of their body weight in conjunction with this change in body composition—and this was achieved without diet or exercise. (See FIG. 6.)

Example 3: Pharmaceutical Compositions Containing HTA-8

This Example describes the development of a pharmaceutical composition containing HTA-8. In addition to HTA-8, lysine and arginine, the pharmaceutical composition of this Example may contain several other key ingredients with additional, complementary functions, as well as excipients, diluents, preservatives and the like.

Ornithine. Ornithine is an amino acid acting as a powerful releasing factor for GH, that is known to work well in combination with lysine and arginine.

$GHRF_2$. $GHRF_2$ is predominantly responsible for stimulating the liver's synthesis and secretion of IGF-2. This second insulin-like growth factor has a greater affinity than IGF-1 for bone marrow receptors that stimulate immune cell function and osteoblast receptors that stimulate an increase in bone density. The competition between IGF-2 and IGF-1 actually releases more IGF-1 to target cells that IGF-1 has a greater affinity for than IGF-2, such as the skeletal muscle mass and the skin.

Melatonin. The principal accepted application of melatonin is to decrease the amount of time that it takes to fall asleep and to increase the duration and quality of restful sleep. By including melatonin in the HTA-8 formulation, there is an improvement in sleep patterns which also assists the natural nocturnal release of GH.

DHEA. DHEA is the adrenal gland precursor to the sex hormones testosterone, estrogen and progesterone. Proponents of DHEA report that the steroid has a basic anti-aging influence. Recent studies have shown that DHEA supplementation helps to restore muscle mass and decrease adipose tissue mass, and decrease total serum cholesterol.

L-Glutamine. L-Glutamine has excellent anti-aging and stress reduction properties. As an oral supplement, glutamine has been shown to work as an effective anti-oxidant, strengthen immunity, cut illness short, aid in recovery from illness, and rejuvenate muscles weakened by stress and illness.

Calcium, Iron, Magnesium coenzyme minerals. These minerals need to be present as cofactors that permit the secretion of GH.

HTA-8 Formulation

| Ingredients | Quantity | Range |
| --- | --- | --- |
| Deionized Water | 97,807.840 gm | |
| L-Lysine | 380.000 gm | 200-500 gm |
| L-Arginine HCl | 380.000 gm | 200-500 gm |
| L-Ornithine | 380.000 gm | 200-500 gm |
| Pyridoxine HCl | 380.000 gm | 200-500 gm |
| Melatonin | 10.000 gm | 1-20 gm |
| Sodium Chondroitin Sulfate | 10.000 gm | 1-20 gm |
| L-Glutathione | 380.000 gm | 200-500 gm |
| HTA-8 | 0.005 gm | 0.001-0.010 gm |
| Potassium Sorbate | 22.680 gm | |
| Sodium Benzoate | 22.680 gm | |
| Benzyl Alcohol | 113.400 gm | |
| Methylparaben | 113.400 gm | |

Recommended Dosage & Instructions for Administration

Oral Spray: Administer one spray of the HTA-8 pharmaceutical corn position to the back of the mouth in the morning, and two sprays in the evening prior to bed. Abstain from drinking or eating for at least 10 minutes after administration.

Example 4: Oral Absorption of HTA-8 Versus HGH in an Oral Spray

Oral absorption of HTA-8 is based on the peptide's small size and its ability to be readily absorbed through the oral mucosa. HGH, on the other hand, is not readily absorbed through the intact oral mucosa because HGH is a 191 amino acid protein, and the upper threshold of trans-mucosal absorption for peptides is around 60 amino acids.

In addition to HGH's large size as a prohibitive factor for an oral spray formulation, it should also be understood that HGH in liquid form is extremely unstable. Consequently, although the concentration of HGH placed in solution at the time of manufacture may be substantial, final levels of HGH by the time the product gets into the hands of the end consumer will be very low. At this time, there is no reliable technology available to stabilize HGH in solution.

Including a relatively small sugar/protein transport molecule called a glycosaminoglycan, or GAG molecule, in the formulation, assists HTA-8 transmucosal absorption, and also helps to stabilize HTA-8 in the formulation. HTA-8 was attached to a GAG molecule(s) to form a proteoglycan in all clinical trials. Proteoglycan formation is discussed, for example, in Hileman et al., *Glycosaminoglycan-protein interactions: definition of consensus sites in glycosaminoglycan binding proteins*, BioEssays, 20, 156-167 (1998), which is hereby incorporated by reference in its entirety.

Example 5: HTA-8 Pharmaceutical Composition Versus HGH Supplementation

The HTA-8 pharmaceutical composition is ideal for those individuals whose objective is to benefit from an increase in their body's own release of GH without the hassles of typical HGH supplementation. In particular:

HTA-8 formulation users will never have to be concerned by the need for injections that are required with HGH. A simple intra-oral spray or effervescent tablet releases enough HTA-8 to stimulate the body's own synthesis and secretion of GH.

HTA-8 formulation use will not suppress the body's natural cyclical release of GH, as is commonly the case with HGH supplementation.

Consequently, a subject may start and stop the use of the HTA-8 formulation without risk.

HTA-8 formulation users can comfortably use HTA-8 in the absence of physician supervision because HTA-8 does not expose the body to the pharmacologic concentrations of GH commonly used with HGH injections.

STATEMENTS REGARDING INCORPORATION BY REFERENCE AND VARIATIONS

All references cited throughout this application, for example patent documents including issued or granted patents or equivalents; patent application publications; and non-patent literature documents or other source material; are hereby incorporated by reference herein in their entireties, as though individually incorporated by reference.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments, exemplary embodiments and optional features, modification and variation of the concepts herein disclosed can be resorted to by those skilled in the art, and that such modifications and variations are considered to be within the scope of this invention as defined by the appended claims. The specific embodiments provided herein are examples of useful embodiments of the invention and it will be apparent to one skilled in the art that the invention can be carried out using a large number of variations of the devices, device components, and method steps set forth in the present description. As will be apparent to one of skill in the art, methods and devices useful for the present methods and devices can include a large number of optional composition and processing elements and steps.

When a group of substituents is disclosed herein, it is understood that all individual members of that group and all subgroups are disclosed separately. When a Markush group or other grouping is used herein, all individual members of the group and all combinations and subcombinations possible of the group are intended to be individually included in the disclosure.

It must be noted that as used herein and in the appended claims, the singular forms "a", "an", and "the" include plural reference unless the context clearly dictates otherwise. Thus, for example, reference to "a peptide" includes a plurality of such peptides and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described. Nothing herein is to be construed as an admission that the invention is not entitled to antedate such disclosure by virtue of prior invention.

Whenever a range is given in the specification, for example, a range of integers, a temperature range, a time range, a composition range, or concentration range, all intermediate ranges and subranges, as well as all individual values included in the ranges given are intended to be included in the disclosure. As used herein, ranges specifically include the values provided as endpoint values of the range. As used herein, ranges specifically include all the integer values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous and can be used interchangeably with "including," "containing," or "characterized by," and is inclusive or open-ended and does not exclude additional, unrecited elements or method steps.

As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" can be replaced with either of the other two terms. The invention illustratively described herein suitably can be practiced in the absence of any element or elements, limitation or limitations which is/are not specifically disclosed herein.

All art-known functional equivalents of materials and methods are intended to be included in this disclosure. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments and optional features, modification and variation of the concepts herein disclosed can be resorted to by those skilled in the art, and that such modifications and variations are considered to be within the scope of this invention as defined by the appended claims.

What is claimed is:

1. A growth hormone releasing factor (GHRF) analog comprising a sequence of $Xaa_1$-D-2-Nal-Trp-His-Trp-D-Phe-$Xaa_2$, wherein $Xaa_1$ is an amino acid residue selected from D-Ala, D-Val and Gly and $Xaa_2$ is an amino acid residue selected from Lys and Arg, or a pharmaceutically acceptable salt thereof.

2. The GHRF analog of claim 1, wherein $Xaa_1$ is an amino acid residue selected from D-Ala and D-Val.

3. The GHRF analog of claim 1, wherein $Xaa_1$ is D-Ala.

4. The GHRF analog of claim 1, wherein $Xaa_1$ is D-Ala and $Xaa_2$ is Lys.

5. The GHRF analog of claim 1 having an optical purity of at least 90%.

6. The GHRF analog of claim 1, wherein the GHRF analog is formulated as a conjugate.

7. The GHRF analog of claim 6, wherein the GHRF analog is conjugated to a compound selected from the group consisting of glycosaminoglycans (GAGs), glycosaminoglycan-like (GAG-like) polysaccharides, oligosaccharides and combinations thereof.

8. A pharmaceutical composition comprising the GHRF analog of claim 1 and one or more pharmaceutically acceptable carriers, excipients and/or diluents.

9. The pharmaceutical composition of claim 8, further comprising one or more amino acids.

10. The pharmaceutical composition of claim 9, wherein the amino acid(s) is/are present in a concentration from 300 mg to 600 mg.

11. The pharmaceutical composition of claim 9, wherein the amino acid(s) is/are selected from the group consisting of lysine, argenine, ornithine, glutamine and combinations thereof.

12. A pharmaceutical composition comprising the GHRF analog of claim 6 and one or more pharmaceutically acceptable carriers, excipients and/or diluents.

13. The pharmaceutical composition of claim 12, further comprising one or more amino acids.

14. The pharmaceutical composition of claim 13, wherein the amino acid(s) is/are present in a concentration from 100 mg to 500 mg.

15. The pharmaceutical composition of claim 13, wherein the amino acid(s) is/are selected from the group consisting of lysine, argenine, ornithine, glutamine and combinations thereof.

16. A method of inducing growth hormone secretion in a subject in need thereof, said method comprising administering to said subject a therapeutically effective amount of the GHRF analog of claim 1 or a conjugate or pharmaceutically acceptable salt thereof.

17. The method of claim 16, wherein said GHRF analog, conjugate or pharmaceutically acceptable salt is administered at a daily dose of 100 ng/Kg to 500 ng/Kg.

18. The method of claim 16, wherein said GHRF analog, conjugate or pharmaceutically acceptable salt is administered orally or mucosally.

19. The method of claim 16, wherein the GHRF analog, conjugate or pharmaceutically acceptable salt is administered as an oral spray or effervescent tablet.

* * * * *